US00PP19374P2

(12) United States Plant Patent
Smith

(10) Patent No.: US PP19,374 P2
(45) Date of Patent: Oct. 21, 2008

(54) ***PAEONIA* PLANT NAMED 'SINGING IN THE RAIN II'**

(50) Latin Name: ***Paeonia lactiflora*×(*Paeonia lutea*× *Paeonia suffruticosa*)**
Varietal Denomination: Singing In The Rain II

(76) Inventor: Donald Robert Smith, 46 Exeter St., W. Newton, MA (US) 02465

( * ) Notice: Subject to any disclaimer, the term of this patent is extended or adjusted under 35 U.S.C. 154(b) by 0 days.

(21) Appl. No.: 12/011,389

(22) Filed: Jan. 25, 2008

(51) Int. Cl.
*A01H 5/00* (2006.01)

(52) U.S. Cl. ..... Plt./316

(58) Field of Classification Search ..... Plt./316
See application file for complete search history.

*Primary Examiner*—Annette H Para
(74) *Attorney, Agent, or Firm*—C. A. Whealy

(57) ABSTRACT

A new and distinct cultivar of *Paeonia* plant named 'Singing In The Rain II', characterized by its compact and symmetric globular plant habit; vigorous growth habit; narrow and finely-divided foliage; freely flowering habit; bright yellow-colored flowers that are initially suffused with deep pink when opening and are arranged on strong peduncles just above and beyond the foliage; long flowering period; and good garden performance.

2 Drawing Sheets

Botanical designation: *Paeonia lactiflora*×(*Paeonia lutea*×*Paeonia suffruticosa*).
Cultivar denomination: 'Singing In The Rain II'.

BACKGROUND OF THE INVENTION

The present invention relates to a new and distinct cultivar of *Paeonia,* botanically known as *Paeonia lactiflora*× (*Paeonia lutea*×*Paeonia suffruticosa*) and hereinafter referred to by the name 'Singing In The Rain II'.

The new *Paeonia* is a naturally-occurring division mutation of the *Paeonia lactiflora*×(*Paeonia lutea*×*Paeonia suffruticosa*) cultivar Singing In The Rain, not patented. The new *Paeonia* was discovered and selected by the Inventor as a single plant in a population of plants of the parent selection in a controlled environment in Windham, N.H. during the spring of 2003. The new *Paeonia* was selected based on its plant growth habit.

Asexual reproduction of the new cultivar by tissue culture in L'Assomption, Quebec, Canada, since the fall of 2003, has shown that the unique features of this new *Paeonia* are stable and reproduced true to type in successive generations.

SUMMARY OF THE INVENTION

Plants of the cultivar Singing In The Rain II have not been observed under all possible environmental conditions. The phenotype may vary somewhat with variations in environment such as temperature and light intensity without, however, any variance in genotype.

The following traits have been repeatedly observed and are determined to be the unique characteristics of 'Singing In The Rain II'. These characteristics in combination distinguish 'Singing In The Rain II' as a new and distinct cultivar:

1. Compact and symmetric globular plant habit.
2. Vigorous growth habit.
3. Narrow and finely-divided foliage.
4. Freely flowering habit.

5. Bright yellow-colored flowers that are initially suffused with deep pink when opening and are arranged on strong peduncles just above and beyond the foliage.
6. Long flowering period.
7. Good garden performance.

Plants of the new *Paeonia* differ primarily from plants of the parent, the cultivar Singing In The Rain, in the following characteristics:

1. Plants of the new *Paeonia* are more compact and more upright than plants of the cultivar Singing In The Rain.
2. Plants of the new *Paeonia* have more finely-dissected leaves than plants of the cultivar Singing In The Rain.

Plants of the new *Paeonia* can be compared to plants of the *Paeonia* cultivar Garden Treasure, disclosed in U.S. Plant Pat. No. 5,718. In side-by-side comparisons conducted by the Inventor in Windham, N.H., plants of the new *Paeonia* differed from plants of the cultivar Garden Treasure in the following characteristics:

1. Plants of the new *Paeonia* were more compact and more globular than plants of the cultivar Garden Treasure.
2. Plants of the new *Paeonia* had stronger flowering stems than plants of the cultivar Garden Treasure.
3. Plants of the new *Paeonia* had narrower and more finely-dissected leaves than plants of the cultivar Garden Treasure.
4. Plants of the new *Paeonia* were more freely flowering than plants of the cultivar Garden Treasure.
5. Plants of the new *Paeonia* flowered earlier than plants of the cultivar Garden Treasure.
6. Plants of the new *Paeonia* had smaller flowers with fewer petals per flower than plants of the cultivar Garden Treasure.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Paeonia*.

The photograph on the first sheet comprises a side perspective view of a typical flowering plant of 'Singing In The Rain II' grown in an outdoor nursery.

The photograph on the second sheet is a close-up view of a typical flower of 'Singing In The Rain II'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the early spring and summer in an outdoor nursery in Windham, N.H. for about four years. During the production of the plants, day temperatures ranged from 3° C. to 32° C. and night temperatures ranged from 1° C. to 20° C.

Botanical classification: *Paeonia lactiflora*×(*Paeonia lutea*×*Paeonia suffruticosa*) cultivar Singing In The Rain II.

Parentage: Naturally-occurring division mutation of the *Paeonia lactiflora*×(*Paeonia lutea*×*Paeonia suffruticosa*) cultivar Singing In The Rain, not patented.

Propagation:

*Type.*—By tissue culture.

*Root description.*—Fleshy, thick; 166C to 166D in color.

*Rooting habit.*—Freely branching; dense.

Plant description:

*Form.*—Perennial subshrub. Compact and symmetric globular plant habit. Vigorous growth habit.

*Plant height.*—About 68 cm to 76 cm.

*Plant width.*—About 105 cm to 115 cm.

Foliage description:

*Arrangement.*—Alternate, bi-ternately compound with about nine leaflets per leaf.

*Leaf length.*—About 23 cm.

*Leaf width.*—About 30 cm.

*Leaflet length.*—About 5 cm to 11 cm.

*Leaflet width.*—About 4 cm to 9 cm.

*Leaflet shape.*—Elliptical.

*Leaflet apex.*—Broadly acuminate often with multiple teeth.

*Leaflet base.*—Attenuate.

*Leaflet margin.*—Smoothly incised.

*Leaflet texture, upper and lower surfaces.*—Smooth, glabrous.

*Leaflet venation pattern.*—Pinnate; reticulate.

*Leaflet color.*—Developing foliage, upper surface: 146C overlaid with 46A. Developing foliage, lower surface: 147C overlaid with 46A. Fully expanded foliage, upper surface: 137A; occasionally towards the apices, 183A; venation, 145A. Fully expanded foliage, lower surface: 191A; venation, 145A.

*Petiole length.*—About 4 cm to 9 cm.

*Petiole diameter.*—About 6 mm.

*Petiole texture, upper and lower surfaces.*—Smooth, glabrous.

*Petiole color, upper surface.*—145A to 145B; venation, between 182B and 181B.

*Petiole color, lower surface.*—144A; venation, 144A.

Flower description:

*Flower arrangement and shape.*—Semi-double cupped flowers. Flowers face upright to outward and are arranged on strong peduncles just above and beyond the foliage. Freely flowering habit, about 60 to 100 flowers develop per plant.

*Natural flowering season.*—Continuous flowering from late spring to early summer in New Hampshire.

*Flower longevity on the plant.*—About six days; flowers not persistent.

*Fragrance.*—Mild, lemon-like.

*Flower buds.*—Length: About 2.8 cm to 3 cm. Diameter: About 2.6 cm to 2.8 cm. Shape: Globose with cuspidate apex. Color: 144A to 144B; typically flushed with 183C to 183D.

*Flowers.*—Diameter: about 12.7 cm to 15.2 cm. Depth (height): About 5 cm.

*Petals.*—Arrangement: About 12 to 26 in several imbricate whorls. Length: About 7 cm. Width: About 5.4 cm to 5.7 cm. Shape: Rounded to nearly cordate. Apex: Emarginate with pronounced V-shaped central notch. Margin: Entire, sinuate or lobed. Texture, upper and lower surfaces: Smooth, glabrous. Color: When opening, upper and lower surfaces: 4C overlaid with 48B. Fully opened, upper and lower surfaces: 4B; occasional streaks, 61A.

*Sepals.*—Arrangement: Three in a single whorl. Length: About 2.9 cm. Width: About 3.8 cm. Shape: Obcordate to obovate. Apex: Mucronate. Base: Truncate. Margin: Entire. Texture, upper and lower surfaces: Smooth, glabrous. Color, upper surface: 144A to N144B. Color, lower surface: 144A to 144B.

*Peduncles.*—Length: About 72 cm. Diameter: About 1 cm. Strength: Strong. Texture: Smooth, glabrous. Color: 144A.

*Reproductive organs.*—Stamens: Quantity per flower: About 50 to 70. Filament length: About 1.3 cm. Filament color: 9A. Anther shape: Elongated ovoid. Anther length: About 1.5 mm to 4 mm. Anther color: 14A. Pollen amount: Scarce. Pollen color: 14A. Pistils: Quantity per flower: About three or four. Pistil length: About 2.2 cm to 2.5 cm. Stigma shape: Claw-shaped, acutely convex. Stigma color: 11A. Ovary color: 137B.

*Seed/fruit.*—Seed and fruit production has not been observed.

Disease resistance: Plants of the new *Paeonia* have been observed to be resistant to Leaf Spot and Powdery Mildew.

Garden performance: Plants of the new *Paeonia* have good garden performance and have exhibited good tolerance to rain and wind and have been observed to tolerate temperatures from about −30° C. to about 37° C.

It is claimed:

1. A new and distinct *Paeonia* plant named 'Singing In The Rain II' as illustrated and described.

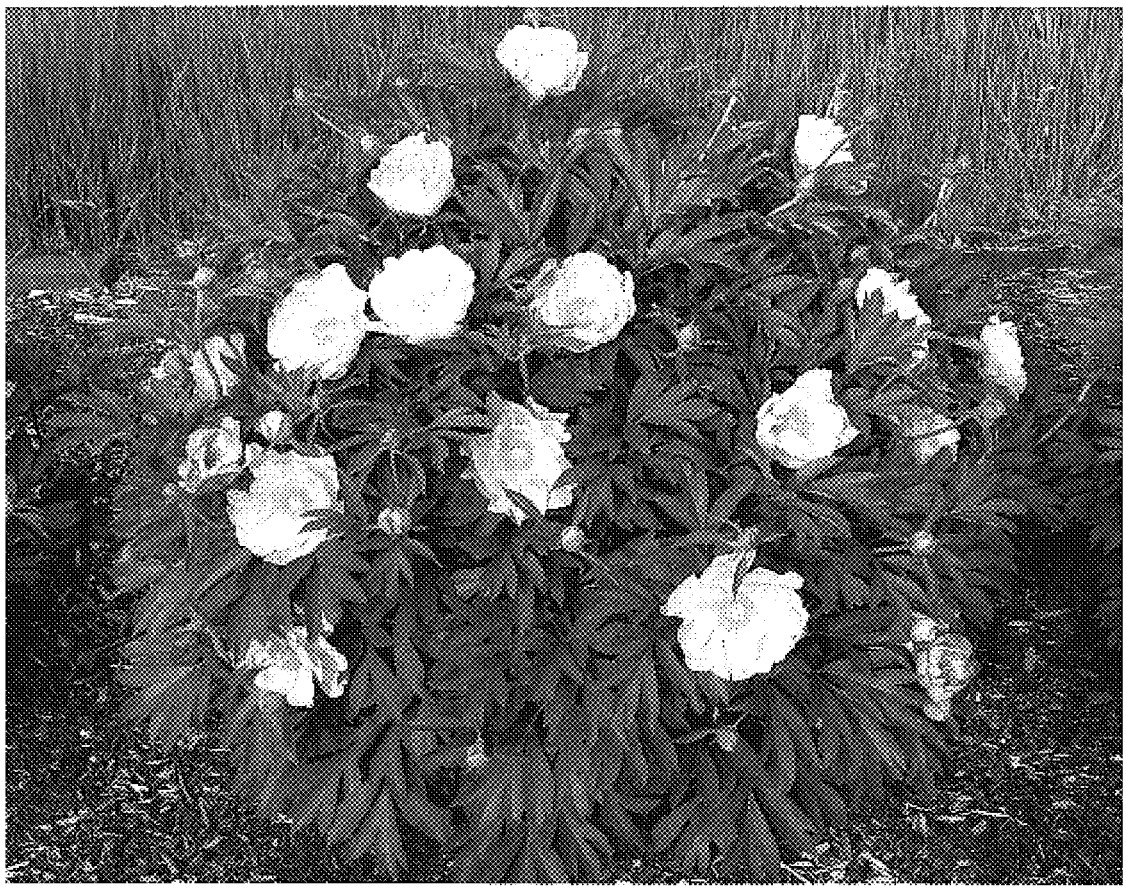

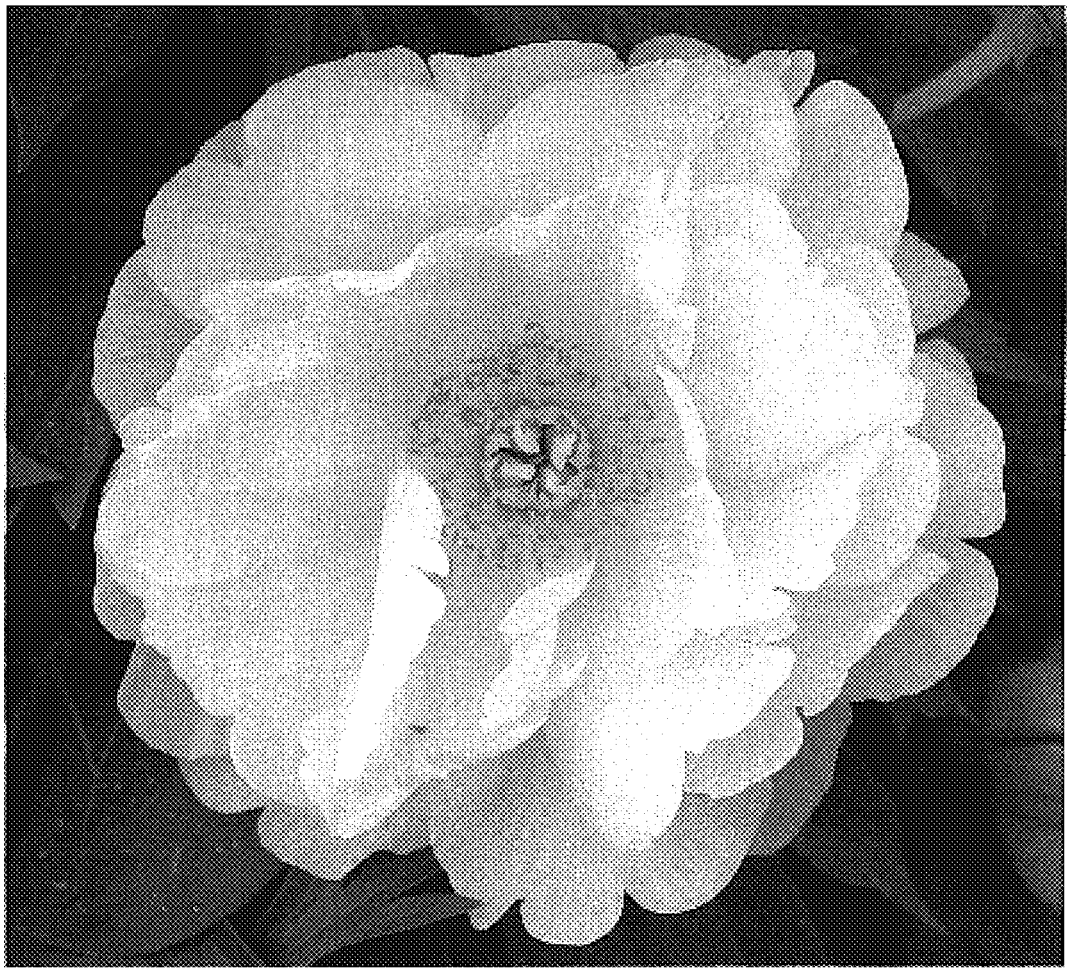

* * * * *